(12) United States Patent
Aydelott et al.

(10) Patent No.: US 6,760,403 B2
(45) Date of Patent: Jul. 6, 2004

(54) METHOD AND APPARATUS FOR ORIENTING A CRYSTALLINE BODY DURING RADIATION DIFFRACTOMETRY

(75) Inventors: Richard M. Aydelott, Ridgefield, WA (US); Mark E. Secrest, Vancouver, WA (US)

(73) Assignee: SEH America, Inc., Vancouver, WA (US)

( * ) Notice: Subject to any disclaimer, the term of this patent is extended or adjusted under 35 U.S.C. 154(b) by 148 days.

(21) Appl. No.: 10/003,881

(22) Filed: Oct. 25, 2001

(65) Prior Publication Data

US 2003/0081723 A1 May 1, 2003

(51) Int. Cl.[7] ............................................. G01N 23/20
(52) U.S. Cl. .......................................... 378/79; 378/70
(58) Field of Search .............................. 378/79, 70, 71, 378/73, 81

(56) References Cited

U.S. PATENT DOCUMENTS

| | | | |
|---|---|---|---|
| 2,431,282 A | * 11/1947 | Speed | 125/35 |
| 2,585,916 A | * 2/1952 | Coleman | 378/78 |
| 2,973,687 A | 3/1961 | Pennington et al. | |
| 3,124,638 A | 3/1964 | Loro | |
| 4,002,410 A | 1/1977 | Frederick et al. | |
| 4,634,490 A | 1/1987 | Tatsumi et al. | |
| 4,710,259 A | * 12/1987 | Howe et al. | 117/15 |
| 4,771,446 A | 9/1988 | Howe et al. | |
| 4,788,702 A | 11/1988 | Howe et al. | |
| 4,862,488 A | 8/1989 | Schiller | |
| 4,910,758 A | 3/1990 | Herrick | |
| 4,995,063 A | 2/1991 | Enoki et al. | |
| 5,073,918 A | 12/1991 | Kamon | |
| 5,148,457 A | 9/1992 | Kubota et al. | |
| 5,187,729 A | 2/1993 | Ibe et al. | |
| 5,720,271 A | 2/1998 | Hauser | |
| 5,768,335 A | 6/1998 | Shahid | |
| 5,876,819 A | 3/1999 | Kimura et al. | |

* cited by examiner

*Primary Examiner*—Louis M. Arana
(74) *Attorney, Agent, or Firm*—Alston & Bird LLP

(57) ABSTRACT

The method and apparatus of the present invention permit indirect identification of a target plane, such as the plane identified by an alignment feature, based upon the identification of a reference plane which is offset by a predetermined angle from the target plane. In addition, in order to permit alignment features to be defined at non-standard angles with respect to the axial orientation of an ingot, an apparatus is provided that includes a frame having at least two members. The first member abuts a bar extending outwardly from the stage of an x-ray diffractometer, while the second member carries an engagement member for engaging a non-standard alignment feature. The second member may be movable relative to the first member to permit the frame to be mounted upon ingots having different non-standard alignment features.

19 Claims, 6 Drawing Sheets

METHOD AND APPARATUS FOR ORIENTING A CRYSTALLINE BODY DURING RADIATION DIFFRACTOMETRY

FIELD OF THE INVENTION

The present invention relates generally to the manufacture of crystalline bodies, such as crystalline ingots, and, more particularly, to methods and apparatus for orienting a crystalline body during radiation diffractometry, such as for purposes of initially identifying the location at which an alignment feature, such as a flat or a notch, is to be formed or for thereafter verifying the location of the alignment feature.

BACKGROUND OF THE INVENTION

The crystalline bodies that are grown, generally in the form of crystalline ingots, during the process of manufacturing semiconductor wafers are crystalline structures. In this regard, the ingots have a predefined crystal orientation in the axial direction, such as an <100> axial orientation. During a number of subsequent manufacturing operations, the position of the ingot as well as the wafers that are subsequently formed from the ingot with respect to a target plane location, must be precisely determined. For example, other material layers must generally be grown, deposited or otherwise formed upon the wafer in a predetermined manner with respect to the target plane. As known to those skilled in the art, the target plane location is related to the axial orientation in that the relative positional relationship of a family of target planes are defined by the axial orientation. In other words, the axial orientation provides information relating to the angular spacing of a family of target planes, but does not dictate the particular location of any of the target planes. For example, wafers formed from an ingot having an <100> axial orientation will have a family of four {110} planes separated by 90° from one another; any one of which may serve as the target plane.

In order to facilitate proper positioning of the ingot or wafer during subsequent manufacturing operations, an alignment feature, such as a notch or a flat, is typically formed lengthwise along the ingot or more commonly along a block or segment of the ingot (hereinafter collectively referred to as an ingot). By directly identifying the location of the target plane with the alignment feature, subsequent manufacturing operations can be referenced to the alignment feature and, in turn, to the target plane. Alignment features are well known with a flat being typically formed to be parallel to the target plane. In contrast, a notch is typically formed such that a radial line that bisects the notch is perpendicular to the target plane.

In order to form the alignment feature in a desired location, the crystalline body is typically examined to identify the target plane location. Typically, the crystalline body is subjected to radiation, such as x-rays, at a variety of incidence angles. The reflected radiation is monitored and the position of the crystalline body at the time at which the intensity or power of the reflected radiation peaks is noted since the peak power or intensity is indicative of reflections from a crystalline plane, such as the crystalline plane that defines the target plane. Once the crystalline plane that defines the target plane has been identified, the alignment feature can be formed lengthwise along the ingot so as to identify the target plane as described above. Secondary alignment features may also be formed lengthwise along the ingot at other predetermined angular positions with respect to the initial or primary alignment features.

In order to identify the crystalline plane 10 that defines the target plane and, in turn, the proper position of the alignment feature 14, the crystalline body 12 is typically placed upon a stage 16 and is illuminated by a radiation source 18, as shown in FIG. 1. The signals reflected or otherwise returning from the crystalline body are captured by a radiation detector 20. While the crystalline body can be placed in various orientations upon the stage, the crystalline body is typically initially positioned upon the stage based upon habit lines that develop during the growth of the crystalline body and that are consistently located in a known manner with respect to the axial orientation. The crystalline body is then moved upon the stage to alter the angle of incidence of the radiation as the radiation source continues to direct radiation to the crystalline body and the radiation detector continues to detect the reflected radiation. For a substantially cylindrical ingot, for example, the ingot is rotated about its longitudinal axis to vary the angle of incidence. Upon detecting the peak of the reflected radiation, the position of the crystalline plane that defines the target plane is identified and the alignment feature is formed so as to directly identify the target plane. While a variety of devices have been developed for examining a crystalline body to determine the location of a target plane, x-ray diffractometers, such as those sold by Rigaku/USA, Inc. of The Woodlands, Tex., are commonly utilized.

After the alignment feature 14 has been formed, such as by grinding a flat or a notch, the crystalline body 12 is typically re-inspected to verify the position of the alignment feature relative to the target plane since the position of the alignment feature to the target plane is critical during subsequent manufacturing operations. This verification is typically performed by again placing the ingot 12 upon the stage 16 and irradiating the ingot. Based upon the alignment feature, the ingot is positioned upon the stage in such a manner that the crystal plane 10 that defines the target plane of the ingot will reflect the incident radiation, thereby maximizing the power or intensity of the reflected radiation. The radiation reflected or otherwise returning from the ingot is detected while the angle of incidence of the radiation is varied slightly, such as by rotating the stage and the ingot relative to the radiation source 18 and detector 20. By determining the peak of the reflected radiation, the position of the target plane and, in turn, the position of the alignment feature relative to the target plane can be confirmed.

In order to facilitate positioning of the ingot 12 and, in particular, the alignment feature 14 of the ingot relative to the underlying stage 16 and, in turn, to the radiation source 18 and detector 20, a fixture 22 is utilized to engage one end of the ingot and to maintain the ingot in a predefined position relative to the underlying stage. As shown in FIG. 1, a fixture generally includes an upstanding plate 24 having a base 26 for contacting a bar 28 that is mounted to and extends upwardly from the stage. The fixture also includes a pair of supports 30, typically in the form of rollers, carried by the plate for engaging circumferential portions of the crystalline ingot. Additionally, the fixture includes an engagement member 32 threadably connected to the edge of the fixture opposite the base for engaging the alignment feature of the ingot. In this regard, the distal end of the engagement member can include a pin for engaging the bottom portion of a notch. Alternatively, the distal end of the engagement member can be planar for engaging a flat. As shown, a conventional fixture therefore engages the alignment feature of a crystalline ingot such that the alignment feature is positioned opposite the bar with the engagement member extending towards the bar in a perpendicular relationship thereto.

Once the end of the crystalline ingot 12 is engaged by the fixture 22, the ingot is irradiated and the radiation reflected by or otherwise returning from the ingot is detected. The stage 16 is then rotated slightly, such as through an angle of about +/−0.5°, in order to vary the angle of incidence and to determine the position of the crystalline ingot that maximizes the reflected radiation. A conventional fixture, such as shown in FIG. 1, is therefore useful in conjunction with crystalline ingots having an alignment feature 14 that directly identifies the crystal plane 10 that defines the target plane by being in a single predetermined position relative to the crystalline body, i.e., relative to the habit lines extending along the length of the crystalline body. For a crystalline body having a <100> axial orientation, for example, the conventional fixture may be configured such that, once the crystalline body is mounted within the fixture based upon the habit lines, a {100} plane will be identified and may be utilized as the target plane by directly identifying the {100} target plane with the alignment feature. However, the fixture does not support the identification of other target planes having different positional relationships with respect to the crystalline body. In this regard, some purchasers of semiconductor wafers are specifying that the alignment feature be defined in non-standard locations, thereby altering the positional relationship of the target plane which defines the location of the alignment feature relative to the crystalline body. For example, some purchasers may require that the alignment feature identify a {111} plane of a crystalline body having a <110> axial orientation.

In order to utilize a conventional fixture, such as the fixture 22 depicted in FIG. 1, to analyze a crystalline body having an alignment feature in a non-standard location, the source of radiation and the radiation detector would have to be modified to irradiate the ingot at a different angle relative to the stage and, in turn, relative to the crystalline body, since the fixture will retain the alignment feature in a position directly opposite the bar even though the alignment feature is now defined in a different positional relationship with respect to the crystalline body. Unfortunately, a conventional x-ray diffractometer is not designed to easily facilitate the disassembly and repositioning of the stage holding the ingot and the radiation detector. As such, any attempts to reconfigure the stage and the radiation detector to irradiate a crystalline ingot at a different angle would be a substantial modification and, even if the modification were possible, the resulting device would have to be requalified and recalibrated to ensure proper measurements were obtained. Additionally, the technicians who conduct the radiation diffractometry analysis are not trained to reconfigure the x-ray diffractometer and, therefore, would require substantial training.

As an alternative to reconfiguring an existing device, an additional x-ray diffractometer could be purchased with the source of radiation and the radiation detector designed to be at the desired angle relative to the stage such that the crystalline body could be properly analyzed to determine if the alignment feature is at the desired non-standard angle with respect to the crystal orientation. Each x-ray diffractometer is quite expensive and generally costs several hundred thousand dollars, thereby rendering it prohibitively expensive to purchase an additional device to analyze ingots for each different non-standard position of the alignment feature.

Depending upon the crystal plane that is to be located, conventional radiation diffractometry techniques may have additional difficulties. In this regard, some crystalline planes are asymmetric. For example, for a crystalline body having a <100> axial orientation, two {100} planes are defined at 0° and 180° and two {110} planes are defined at 90° and 270°. In contrast, the <211> orientation is asymmetric and defines crystal planes at +/−54.7° and +/125.3° as shown in FIG. 2. As such, two pairs of <211> crystal planes exist, namely, a first pair at +54.7° and −125.3° and a second pair at −54.7° and +125.3°. In instances in which the alignment feature is to identify a specific pair of the <211> crystal planes, the direct identification of the desired pair of <211> crystal planes is generally unworkable since a technician will be unable to determine which pair of <211> crystal planes was identified by merely examining the peak of the returned radiation over the relatively small range of incidence angles supported by the rotation of the stage.

Still further, the radiation that is reflected and is collected by a radiation detector not only has a primary peak 34 that signifies reflections from the desired crystal plane, but may have a minor or secondary peak 36 at a different wavelength caused by K-alpha II radiation as shown in FIG. 3. As such, some technicians may inadvertently identify the secondary peak as the peak representative of the reflections from the crystal plane of interest and, therefore, improperly determine the location of the crystal plane of interest. The angle or separation between the primary and secondary peaks depends on, among other things, the position of the source of radiation and the radiation detector. In this regard, increases in the angle, termed theta θ as shown in FIG. 1, between the source of radiation and the crystalline plane of interest and, in turn, between the crystalline plane of interest and the radiation detector also increases the angle or separation between the primary and secondary peaks. Thus, the identification of crystal planes having a relatively large angle with respect to the source of radiation and, in turn, with respect to the radiation detector may render it difficult to reliably identify the primary peak of the detected radiation, thereby complicating the identification of the crystal plane of interest.

As such, it would be desirable to develop a more reliable technique for identifying crystal planes within a crystalline body, such as an ingot. In addition, it would be desirable to develop a technique for identifying the crystal plane that defines the target plane of a crystalline body in instances in which the alignment feature is at any of a variety of non-standard positions without modifying existing x-ray diffractometers and without purchasing additional x-ray diffractometers.

SUMMARY OF THE INVENTION

A method and apparatus are therefore provided for orienting a crystalline body during radiation diffractometry which addresses the foregoing drawbacks associated with conventional techniques. In particular, the method and apparatus of the present invention facilitate orientation of a crystalline body even in instances in which the alignment feature is defined at various non-standard angles with respect to the crystalline body. Moreover, the method and apparatus of the present invention can utilize conventional x-ray diffractometry equipment and thereby eliminate any need to alter existing x-ray diffractometry equipment or to purchase additional x-ray diffractometry equipment. Additionally, the method and apparatus of one advantageous aspect of the present invention facilitate the indirect identification of a target plane based upon the identification of a reference plane which is offset by a predetermined angle from the target plane of interest, but which reflects radiation having a more clearly distinguishable peak than the target plane and/or can be utilized to identify a specific pair of crystal planes from among a plurality of asymmetric crystal planes in an unambiguous manner.

According to one embodiment, an improved method and apparatus for orienting a crystalline body during radiation diffractometry are provided. The apparatus includes a frame having a first member adapted to support the frame relative to a source of radiation and a second member moveably connected to the first member. The frame also includes an engagement member carried by the second member for engaging a predetermined portion of the crystalline body, such as an alignment feature of the crystalline body, to thereby define the angle at which the incident radiation will impinge upon the crystalline body. Thus, the second member of the frame can be positioned relative to the first member of the frame based upon a predefined angular offset between a reference plane to be located based upon the reflected radiation and a target plane identified by the alignment feature of a crystalline body.

The first member can include a base for supporting the frame relative to the source of radiation, such as by contacting a bar connected to and extending outwardly from the stage of an x-ray diffractometer. A second member may also define an aperture for viewing the engagement of the predetermined portions of the crystalline body, such as the alignment feature of the crystalline body, by the engagement member. Additionally, the engagement member may be threadably connected to the second member so as to be threadably advanced into contact with the predetermined portion, such as the alignment feature, of the crystalline body. The frame of this embodiment can also include a third member for locking the first and second members in position with respect to one another. Each of the first and second members may include indicia to facilitate positioning of the first and second members relative to one another. A second member may also include at least one support for engaging another portion of the crystalline body.

The apparatus and associated method of this embodiment facilitate an analysis of the position of an alignment feature relative to the crystalline body, even in instances in which the alignment feature is disposed at various non-standard positions. In this regard, the alignment feature of the crystalline body can be angularly offset from the crystal plane, i.e., the reference plane, that the x-ray diffractometer is designed to detect. By adjusting the angular position of the second member relative to the first member, the apparatus and method of this embodiment can accommodate different angular offsets between the orientation feature and the crystal plane detected during x-ray diffractometry.

According to another aspect of the present invention, an apparatus for orienting the crystalline body during radiation diffractometry includes a frame for supporting at least a portion of the crystalline body and including a base adapted to support the frame relative to a source of radiation. For example, the base may contact a bar connected to and extending outwardly from the stage of an x-ray diffractometer or the like. The apparatus also includes an engagement member carried by the frame for engaging a predetermined portion of the crystalline body, such as the alignment feature of the crystalline body. According to this aspect of the present invention, the engagement member extends at a non-orthogonal angle relative to the base.

The frame may have a number of different configurations, depending upon the angular offset between the reference plane to be detected from the reflected radiation and the target plane to be identified. In one embodiment, the frame includes a central portion and at least two arms extending outwardly from the central portion. One of the arms is connected to the base and another of the arms carries the engagement member. The frame may also include a central portion and the first, second and third arms extending outwardly from the central portion. In this embodiment, the first arm is connected to the base and the third arm carries the engagement member. The third arm also defines an axis extending through the central portion and bisecting the angle defined between the first and second arms. While at least one arm may be movable with respect to the remainder of the frame, the arms may be fixed at a predefined angle to accommodate instances in which the alignment feature is repeatedly formed at the same non-standard angle. For example, the arms may be positioned such that the engagement member extends at an angle of 45° with respect to the base. This exemplary embodiment is particularly useful in instances in which a crystalline body having a <100> axial orientation has an alignment feature that defines a {100} crystal plane since the {110} crystal plane and the {111} crystal plane that a conventional x-ray diffractometer is designed to detect are offset by 45°.

According to another aspect of the present invention, a method is provided for indirectly identifying a target plane defined by a crystalline body. For example, the target plane may be the plane defined by the alignment feature of the crystalline body such that the indirect identification of the target plane serves to verify the location of the alignment feature. Alternatively, the indirect identification of the target plane may also identify the location at which the initial or primary alignment feature is to be formed.

According to this aspect, radiation returning from the crystalline body is analyzed to identify a reference plane defined by the crystalline body. Once the reference plane has been identified, the target plane is located based upon a predefined angular offset between the reference plane and the target plane. Thus, the target plane may be indirectly detected by directly detecting the reference plane and then adding or subtracting the predefined angular offset between the reference plane and the target plane. In instances in which the location of an alignment feature is to be verified, the positional relationship of the target plane to the alignment feature may be determined. For example, it may be determined that the alignment feature is properly located if the angular offset between the target plane and the alignment feature is less than a predetermined threshold. Alternatively, in instances in which an initial or primary alignment feature is to be formed, the alignment feature may be formed so as to identify the target plane.

Typically, the crystalline body is irradiated and the radiation that returns from the crystalline body is detected in order to identify the reference plane defined by the crystalline body. In this regard, the radiation that impinges upon the crystalline body is typically directed toward the crystalline body at a plurality of incidence angles. As such, the reference plane may be identified based upon the incidence angle of the radiation at which the radiation having the greatest power is reflected and, in turn, detected.

By indirectly detecting a target plane based upon the detection of a reference plane and the predefined angular offset between the reference plane and the target plane, the method of this aspect to the present invention facilitates the indirect identification of the plane identified by the alignment feature based upon the direct identification of the reference plane, typically the crystal plane that an x-ray diffractometer is adapted to detect without any reconfiguration. Moreover, the method of this aspect of the present invention may facilitate the identification of a target plane in a more reliable manner than attempts to directly identify the target plane since, in some circumstances, the reference plane will reflect radiation having a more clearly distinguishable peak than the target plane that may otherwise reflect radiation in such a manner as to generate a deceptively large secondary peak. Moreover, a target plane that belongs to a family of asymmetric planes may be specifically determined by identifying a reference plane having a predetermined relationship with the target plane, thereby permitting the unambiguous identification of the target plane relative to the other planes in a family of asymmetric planes. Thus, the method and apparatus of the various embodiments of the present invention address the drawbacks identified by prior radiation diffractometry techniques and provide an improved technique for identifying a target plane, such as the crystal plane identified by an alignment feature.

BRIEF DESCRIPTION OF THE DRAWINGS

Figure 1:
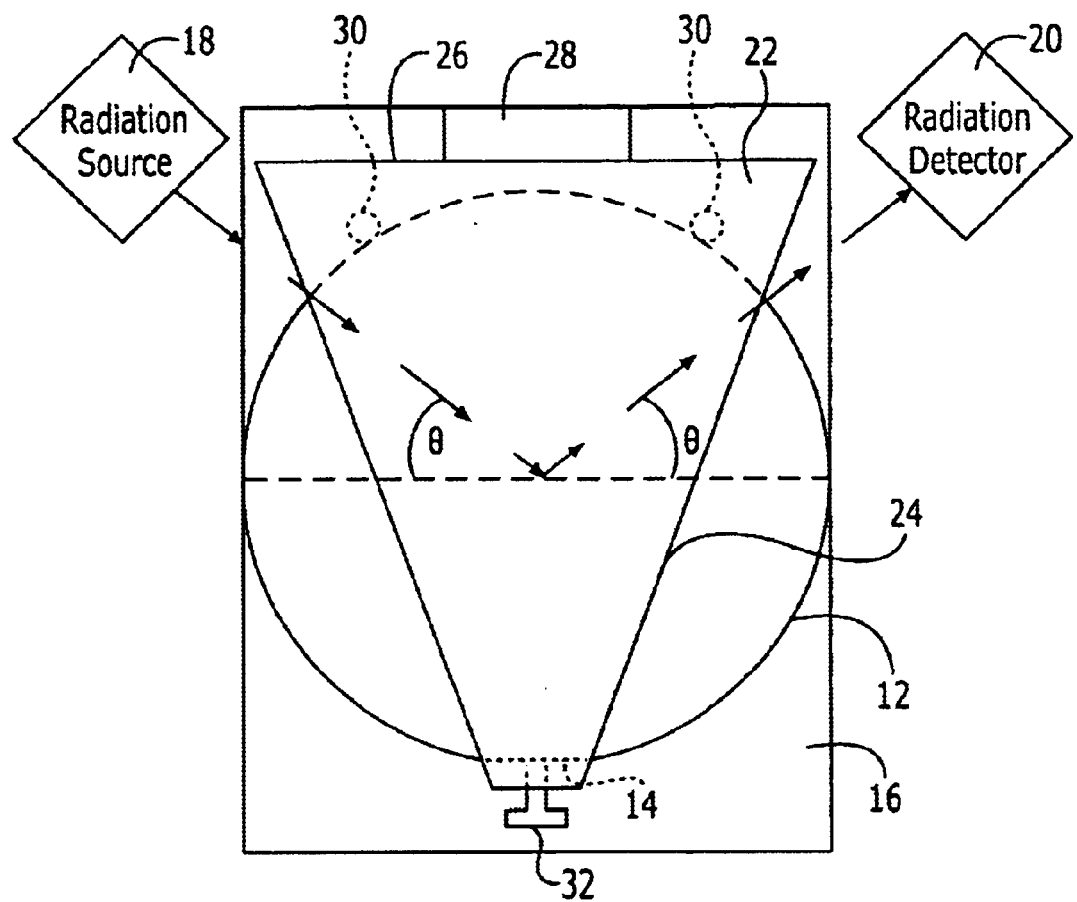
Figure 2:
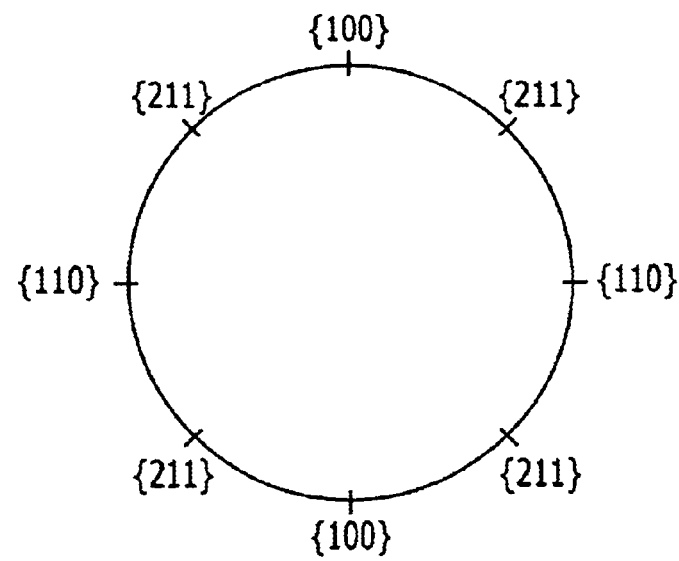
Figure 3:
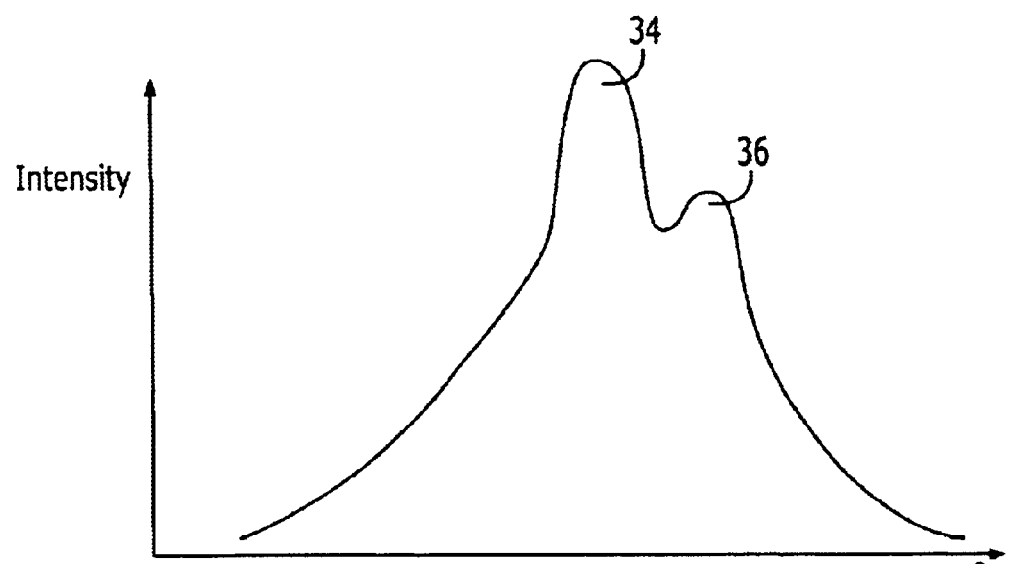
Figure 4:
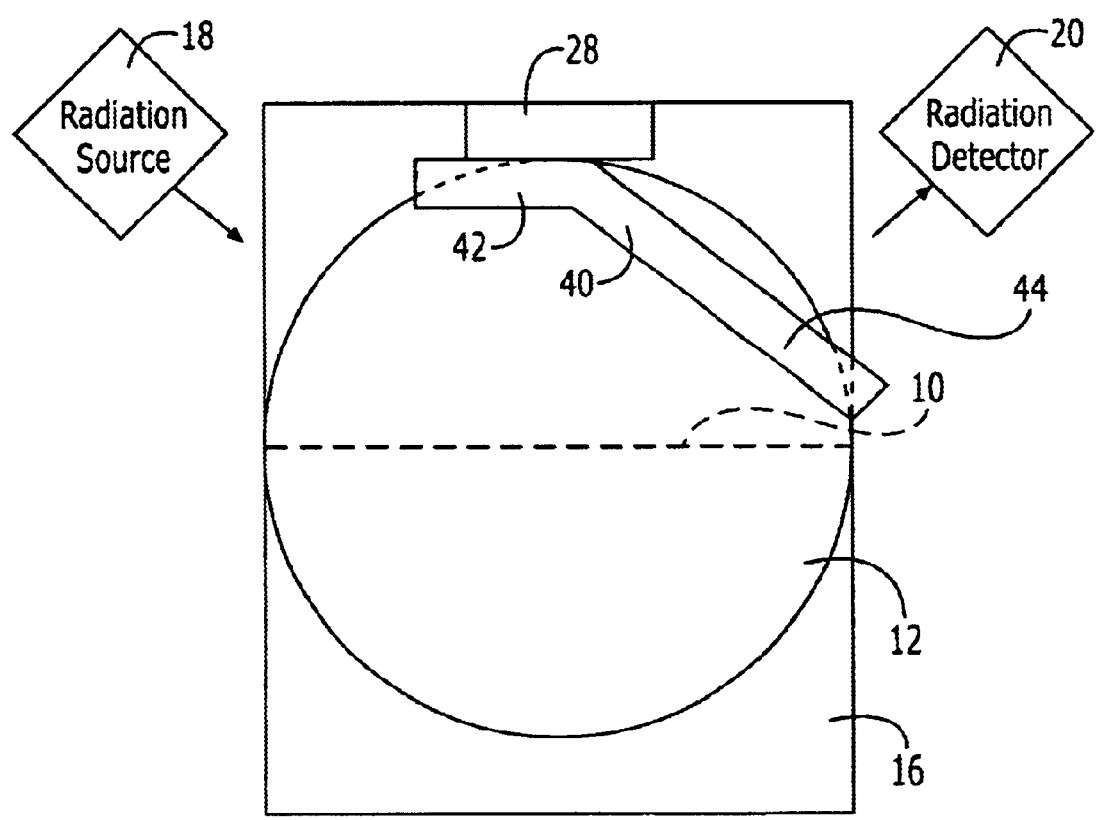
Figure 5:
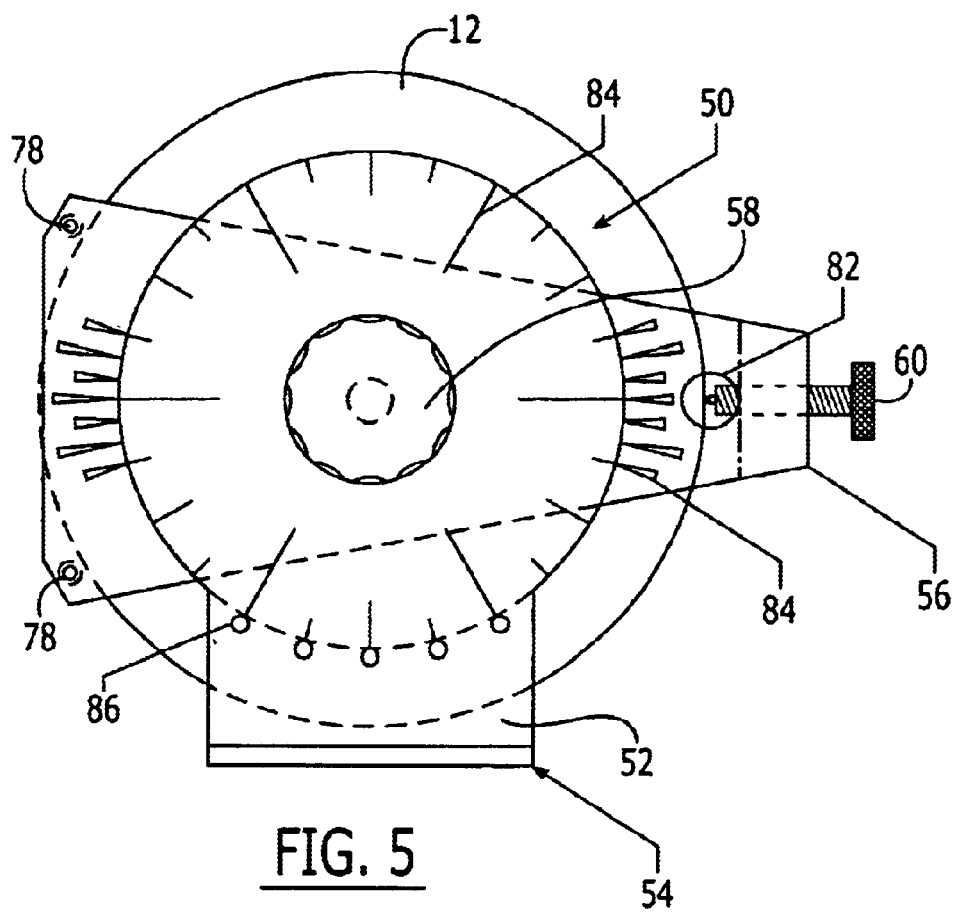
Figure 6:
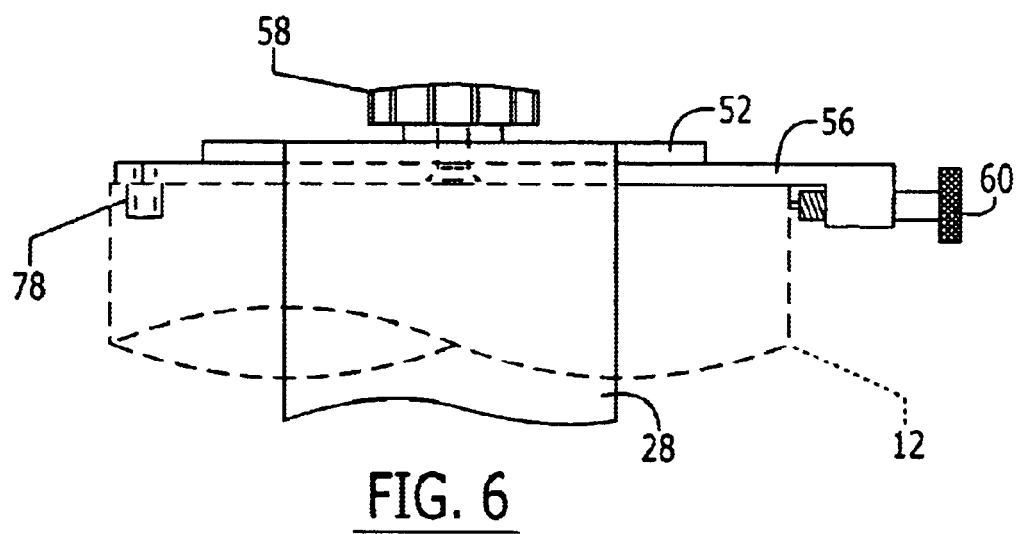
Figure 7:
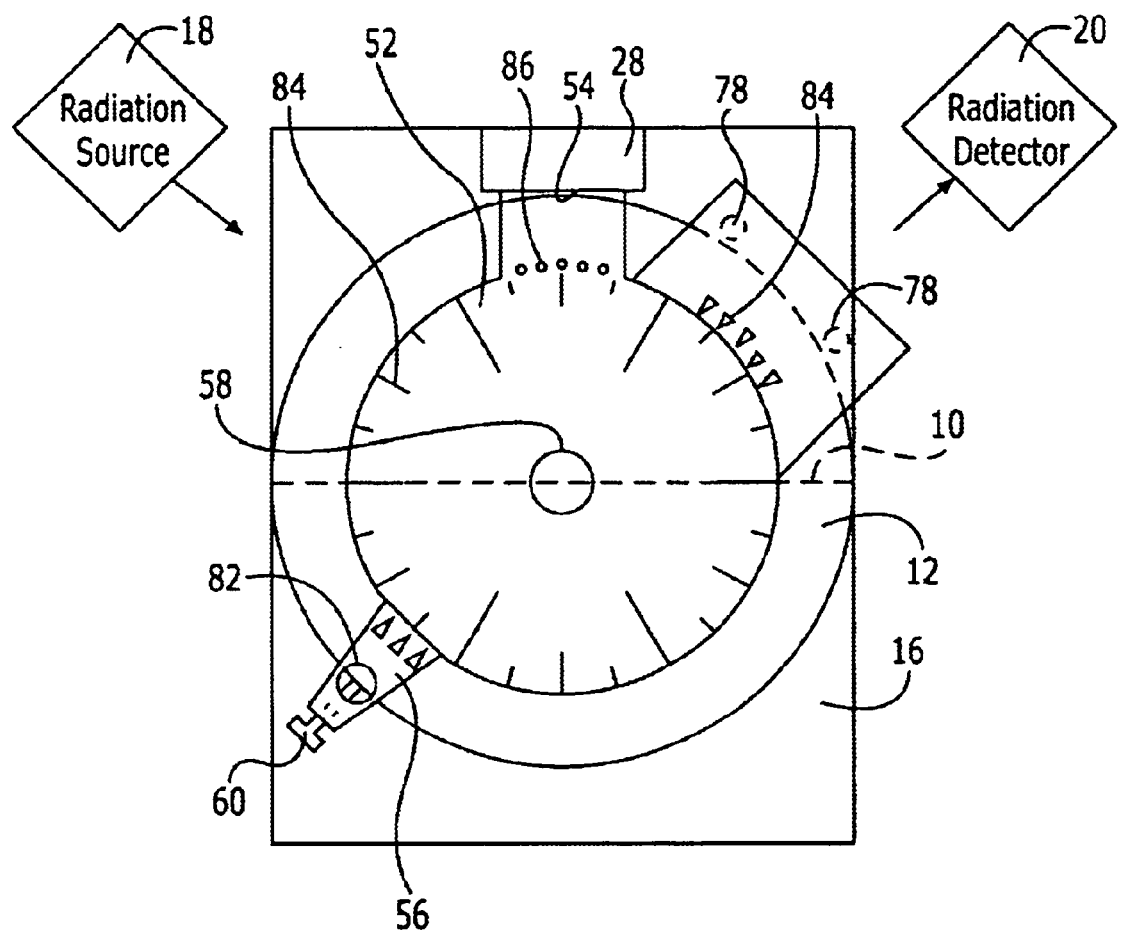
Figure 8:
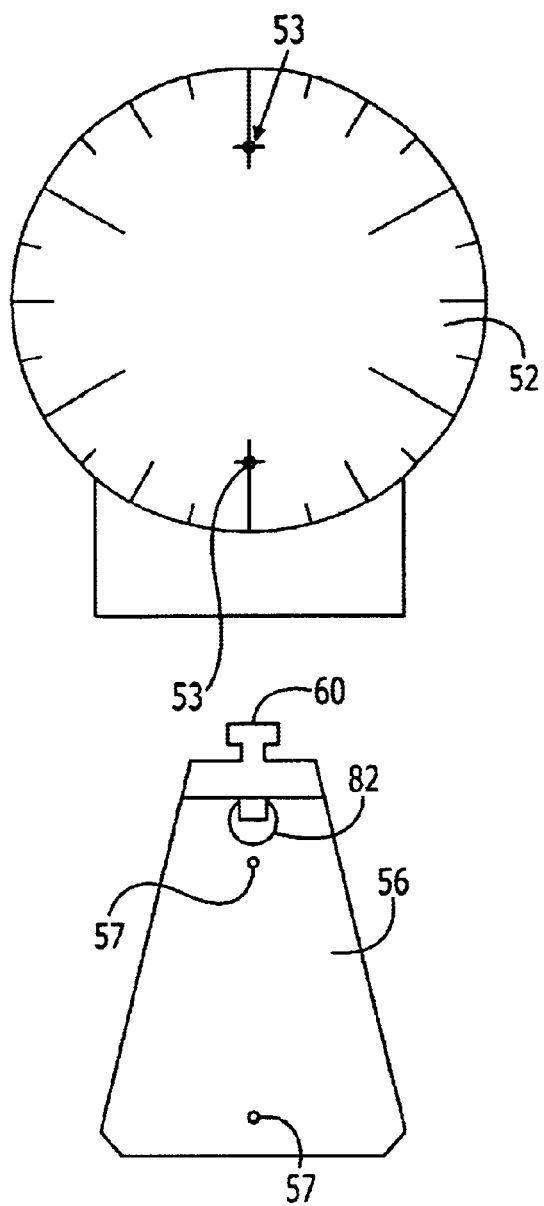
Figure 9:
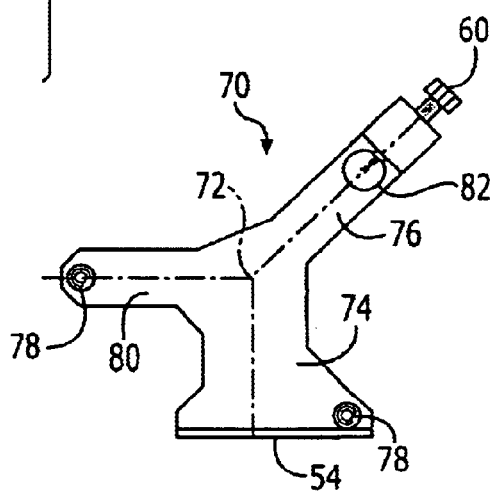

Having thus described the invention in general terms, reference will now be made to the accompanying drawings, which are not necessarily drawn to scale, and wherein:

FIG. 1 is a schematic depiction of an apparatus for performing radiation diffractometry including a conventional fixture for orienting a crystalline body;

FIG. 2 is a graphical depiction of a family of four asymmetric {211} planes relative to a pair of {100} planes and a pair of {110} planes, as defined by a crystalline body having a <110> axial orientation;

FIG. 3 is a graphical representation of the power or intensity of the reflected radiation detected by a radiation detector in response to the illumination of a crystalline body at a variety of incidence angles;

FIG. 4 is a depiction of an angled jig disposed upon an end surface of an ingot to define the location of a target plane that will be marked by an initial or primary alignment feature;

FIG. 5 is a plan view of an apparatus for orienting a crystalline body according to one advantageous embodiment of the present invention;

FIG. 6 is a side view of the apparatus of FIG. 5 in which a fragmentary portion of the crystalline body is depicted in dashed lines;

FIG. 7 is a schematic representation of a system for performing radiation diffractometry including the apparatus of FIG. 5;

FIG. 8 is a plan view of the first and second members of an apparatus according to another embodiment of the present invention; and FIG. 9 is a plan view of an apparatus according to another embodiment to the present invention that is designed to securely hold a crystalline body such that the alignment feature is disposed at an angle of about 45° relative to the base of the frame.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments wet forth herein; rather, these embodiments are provided so that this disclosure will be thorough and complete, and will fully convey the scope of the invention to those skilled in the art. Like numbers refer to like elements throughout.

The method and apparatus of the present invention are preferably designed to identify a reference plane defined by a crystalline body, such as an ingot or a section or block of an ingot, and, based upon the identification of the reference plane, to thereafter identify a target plane that is offset from the reference plane by a predetermined angular amount. As such, the method and apparatus of the present invention facilitate the indirect identification of the target plane in a reliable and accurate manner. As explained in detail below, the reference plane identified by the method and apparatus of the present invention may be the crystal plane that an x-ray diffractometer is adapted to nominally detect and the target plane that is indirectly identified may be the crystal plane defined by the alignment feature. Since the various crystal planes are angularly offset from the one another by predefined angles known to those skilled in the art, the identification of a reference plane can reliably and accurately lead to the indirect identification of the target plane.

The identification of the reference plane is typically performed by irradiating the crystalline body with radiation, such as x-rays, and detecting the radiation reflected or otherwise returning from the crystalline body. In particular, the power or intensity of the radiation reflected or otherwise returning from the crystalline body is monitored. By varying the angle of incidence of the radiation and continuing to monitor the radiation reflected or otherwise returning from the crystalline body, the method and apparatus of the present invention can determine the position of the crystalline body at which the maximum amount of radiation is reflected which, in turn, defines the position of the reference plane. Thereafter, the target plane may be located based upon the location of the reference plane and the predefined angular offset between the reference plane and the target plane.

This indirect identification of the target plane can be utilized in various applications including the initial identification of a target plane, such as the plane to be defined by an initial or primary alignment feature, and the verification of the target plane defined by an existing alignment feature. For example, in order to initially identify a target plane that will thereafter be marked by a primary alignment feature, the crystalline body, such as an ingot, is positioned upon a stage, such as the x-ray stage of a conventional x-ray diffractometer. Since the crystalline body does not yet include an alignment feature, the crystalline body is initially positioned upon the stage based upon the habit lines exhibited by the crystalline body that generally bear a predefined relationship to the reference plane that the x-ray diffractometer is adapted to nominally detect. The crystalline body is then irradiated and the reflected radiation is detected. The crystalline body is typically moved slightly, generally by rotating the stage by +/-0.5°, in order to adjust the angle of incidence while continuing to monitor the reflected radiation such that the position of the crystalline body at which the greatest amount of radiation is reflected or otherwise returned can be determined. Based on the position of the crystalline body at which the greatest amount of radiation is reflected, the reference plane may be determined as known to those skilled in the art. In this regard, the reference plane is defined to be the plane that defines equal angles, theta, with respect to signals transmitted from the radiation source and signals returned to the radiation detector as shown in FIG. 1.

The target plane can then be identified based upon the predetermined angular offset between the reference plane 10 and the target plane. The crystalline body 12 is then marked to identify the location of the reference plane and/or the target plane such that an initial or primary alignment feature, such as a lengthwise extending notch or flat can thereafter be ground to identify the target plane for subsequent alignment purposes. Although the target plane may be identified and the location of the alignment feature marked in various manners, an angled jig 40 may be utilized that has two arms that define an angle equal to the predetermined angular offset between the reference plane and the target plane. As shown in FIG. 4, the angled jig may be placed on an end surface of the ingot with a first arm 42 contacting the bar 28 that extends upwardly from the stage 16. The second arm 44 of the jig then defines the location of the target plane which may be marked for purposes of identifying the location of the primary alignment feature to be formed lengthwise along the ingot.

In order to subsequently verify the location of the alignment feature, the crystalline body is again typically mounted upon the stage of an x-ray diffractometer. In particular, the crystalline body is preferably mounted upon the stage such that the reference plane is generally parallel to the bar extending outwardly from the stage so as to be detected with only slight adjustments in the angle of incidence of the radiation that impinges upon the crystalline body. The reference plane can then be identified as described above by irradiating the crystalline body and identifying the position of the crystalline body at which the maximum radiation is reflected or otherwise returned from the crystalline body as the stage is rotated, such as by +/−0.5°. The location of the target plane can then be determined based upon the predefined angular offset between the target and reference planes. Thereafter, the method and apparatus can verify that the plane identified by the alignment feature is identical to or sufficiently close to the target plane, i.e., having an angular offset of less than a predetermined threshold, to effectively serve as a reference or index during subsequent manufacturing operations.

In order to orient the crystalline body 12 upon the stage 16 of an x-ray diffractometer or the like, an apparatus 50 according to another aspect of the present invention is provided. In this regard, an apparatus is provided for engaging an alignment feature 14 defined by a crystalline body and for maintaining the plane defined by the alignment feature at any selected angle relative to the incident radiation. Thus, the apparatus of this embodiment is adjustable to allow crystalline bodies having different angular relationships between the reference plane that the x-ray diffractometer is adapted to nominally detect and the target plane defined by the alignment feature to be accommodated by a single fixture without having to reconfigure the x-ray diffractometer or purchase a new x-ray diffractometer.

As shown in FIGS. 5 and 6, the apparatus 50 of this aspect of the present invention includes a frame having a first member 52 adapted to support the frame relative to the source of radiation 18. In this regard, the first member generally includes a base 54 that, in most applications, is placed in operable contact with a bar 28 connected to and extending outwardly from the stage 16 of an x-ray diffractometer or the like. The frame of this advantageous embodiment also includes a second member 56 moveably connected to the first member. As shown, the second member is typically rotatably connected to the first member such that the second member can be selectively positioned relative to the first member and, in turn, relative to the stage upon which the frame is supported. The frame may also include a third member 58 for locking the first and second members in position with respect to one another. In the illustrated embodiment, for example, a third member includes a nut or the like mounted upon a bolt or other threaded fastener that extends through apertures defined by the firs and second members. Once the second member is properly positioned relative to the first member, the third member may be tightened, such as by threadably advancing the nut upon the bolt or other threaded fastener so as to fix the positions of the first and second members relative to one another.

The apparatus 50 of this aspect of the present invention also includes an engagement member 60 carried by the second member 56 for engaging a predetermined portion of the crystalline body 12. Typically, the engagement member is adapted to engage an alignment feature 14 defined by the crystalline body, such as a flat or a notch. Although the engagement member can have various configurations, the engagement member of one embodiment is a threaded member that engages a threaded aperture defined by a distal end of the second member 56. As such, the engagement member of this embodiment can be threadably advanced and retracted relative to the distal end of the second member. In embodiments in which the engagement member is to engage a flat defined by the crystalline body, the engagement member preferably has a planar distal end. However, in instances in which the engagement member is to engage a notch, the distal end of the engagement member preferably includes a pin for engaging a bottom portion of the notch. As a result of the threaded connection between the engagement member and the second member, the apparatus of this aspect of the present invention permits one type of engagement member to be replaced with the other type of engagement member, if the apparatus is to be utilized to evaluate a crystalline body having a different type of alignment feature.

In marked contrast to conventional fixtures 22 in which the engagement member 32 and, in turn, the alignment feature 14 of the crystalline body 12 were positioned opposite the base 26 and, therefore, opposite the bar 28 against which the fixture was abutted, the apparatus 50 of this aspect of the present invention permits the engagement member 60 and, in turn, the alignment feature of the crystalline body to be located at any desired position about the circumference of the crystalline body. Thus, the apparatus of this aspect of the present invention can hold a crystalline body in a desired position, such as with the reference plane substantially parallel to the bar of an x-ray diffractometer such that the incident radiation is most strongly reflected, while permitting the alignment feature to be disposed at any circumferential location about the crystalline body. As described above, the method and apparatus can then directly measure a reference plane 10 and subsequently identify a target plane based on the predetermined angular offset of the reference and target planes. Since the crystal plane defined by the alignment feature is typically the target plane, the second member can be angularly offset from a reference position defined by the first member by the predefined angular offset between the reference and target planes. In this regard, the reference position defined by the first member 52 generally extends in an orthogonal direction from the base 54 of the first member. As an example, if the target plane is offset by 20° from the reference plane, the second arm will similarly be angularly offset by 20° from the reference direction defined by the first member of the frame. Thus, once the apparatus is mounted upon the end portion of the crystalline body and the engagement member carried by the second member engages the alignment feature of the crystalline body, the crystalline body will be held by the apparatus in a position relative to the x-ray diffractometer such that the reference plane of the crystalline body is capable of being readily detected, such as by being substantially parallel to the bar against which the frame is abutted. See, for example, FIG. 7. As shown, the second member 56 can also carry one or more supports 78 for engaging circumferential portions of the crystalline body.

The apparatus 50 of this aspect of the present invention can include various features in order to facilitate its configuration and mounting upon a crystalline body 12. In this regard, the second member 56 may define an aperture 82 proximate the engagement member 60 to permit a technician to view and confirm the engagement of the alignment feature 14 by the engagement member. Additionally, both the first and second members may include indicia, such as a plurality of marks 84, to facilitate the positioning of the second member relative to the first member 52. For example, by aligning respective pairs of the marks on the first and second members, the second member may be positioned so as to define a predetermined angle with respect to the first member. In order to permit the marks on the second member to be seen even in instances in which the base 54 of the first member covers a portion of the second member, a portion of the first member proximate the base may define one or more apertures 86.

The crystalline body 12 is then irradiated by the second source of radiation 18 and the radiation reflected or otherwise returning from the crystalline body is detected by the radiation detector 20. The intensity or power of the radiation that is reflected or otherwise returning from the crystalline body is monitored as the angle of incidence of the radiation with which the crystalline body is impinged is varied slightly, such as through about +/−0.5°. Typically, the variation in the angle of incidence is created by a slight movement or rotation of the stage 16 and, in turn, the ingot carried by the stage relative to the source of radiation and the radiation detector. By identifying the position of the crystalline body that corresponds with the peak in the power or intensity of the radiation reflected or otherwise returning from the crystalline body, the reference plane 10 can be identified in the manner described above in conjunction with FIG. 1. Based upon the predefined angular offset between the reference and target planes, the target plane of the crystalline body can then also be identified and any difference between the target plane and the plane defined by the alignment feature 14 is determined.

After disengaging the apparatus 50 from the crystalline body 12, such as by threadably retracting the engagement member 60, the apparatus can be mounted upon the end portion of another crystalline body. As a result of the capability to move the second member 56 relative to the first member 52, the apparatus can engage and hold crystalline bodies having a number of different predefined angular offsets between the reference and target planes. Thus, the apparatus of the present invention facilitates the continued use of the same x-ray diffractometer even as the positioning of the alignment feature 14 relative to the reference plane varies. In order to ensure that the first and second members of the frame are properly positioned, a jig can be provided for each different angle to be defined by the apparatus of the present invention. In this regard, each jig may include a pair of frame members defining a predetermined interior angle. By placing the frame within the jig and positioning the first and second members to extend alongside the frame members, the first and second members will also define the predetermined interior angle therebetween.

As described above, the apparatus 50 is adjustable to permit the apparatus to support crystalline bodies 12 having any number of different predefined offsets between the reference and target planes. In some instances, however, the apparatus will be designed to support crystalline bodies have a predetermined number of different offsets between the reference and target planes. In these instances, the apparatus may be designed to only permit the first and second members to be positioned relative to one another in a predetermined number of discrete positions, each of which corresponds with a respective offset between the reference and target planes. For example, a family of first members may be provided with each first member adapted to mate with the second member to define a respective offset between the reference and target planes. While the first and second members may mate in various manners, one exemplary first member is depicted in FIG. 8 and defines a pair of holes 53. As such, the second member may include a pair of pins 57 designed to engage the holes, thereby fixing the position of the second member with respect to the first member. The first and second members may then be secured together by tightening the third member 58. In order to support a crystalline body having a different offset between the reference and target planes, the first member may be interchanged for another one of the family that mates with the second member to define the different offset between the reference and target planes.

While the apparatus 50 described above is adjustable to thereby permit the apparatus to support crystalline bodies 12 having different predefined offsets between the reference and target planes, the apparatus of other embodiments includes a frame having a base 54 and an engagement member 60 carried by the frame that extends at a non-orthogonal angle relative to the base, irrespective of whether the frame includes members capable of movement with respect to one another. As shown in FIG. 9, for example, the frame 70 includes a central portion 72 and at least two arms extending outwardly from the central portion. One of the arms 74 is connected to the base and another of the arms 76 carries the engagement member. In addition, the frame includes at least one, and more generally, a pair of supports 78 for engaging other circumferential portions of the crystalline body such that the apparatus can be securely mounted upon one end of the crystalline body.

By way of example, the apparatus 70 of the illustrated embodiment includes first, second and third arms 74, 80, 76 extending outwardly from the central portion 72 with the first arm connected to the base 54, and the third arm carrying the engagement member 60. In order to properly engage the crystalline body, the first and second arms each preferably carry a support 78 for engaging other circumferential portions of the crystalline body. In order to provide relatively even engagement of the crystalline body about its circumference, the third arm preferably defines an axis that extends through the central portion and bisects the angle defined by the first and second arms as indicated by the dashed lines in FIG. 9. As such, the crystalline body is supported in three circumferential locations spaced apart by about 120° degrees.

While the apparatus 70 of this embodiment can be designed such that the engagement member 60 extends at any desired non-orthagonal angle relative to the base 54 of the frame, the apparatus of the illustrated embodiment includes an engagement member extending at an angle of 45° with respect to the base. As such, the apparatus is specifically adapted to hold a crystalline body 12 upon the stage 16 of an x-ray diffractometer or the like such that a reference plane 10 that is offset by 45° from a target plane, such as a plane defined by the alignment feature 14 of the crystalline body, can be detected. In one example, the engagement member of the frame engages an alignment feature that defines the <111> plane. As a result of the offset of 45° between the first and second arms, however, the frame of this exemplary embodiment can hold the crystalline body such that the <100> reference plane that is offset by 45° from the <111> plane will be detected by radiation diffractometry.

Regardless of the configuration, the apparatus and method of the present invention facilitate the location of a target plane based upon the direct identification of a reference plane and the predefined angular offset between the reference and target planes. As such, the apparatus may be adjustable to accommodate crystalline bodies having different angular offsets between the reference and target planes or, alternatively, the apparatus may be static for holding crystalline bodies having a single predefined angular offset between the reference and target planes. By permitting a target plane to be indirectly located based upon the direct identification of a reference plane, the method and apparatus of the present invention permit the radiation diffractometry measurements to be optimized.

For example, the reference plane 10 may be selected such that the signals that are reflected from the reference plane will generate a large primary peak 34 with a much smaller secondary peak 36 spaced apart from the primary peak to facilitate the identification of the primary peak and, in turn, the location of the reference plane. Since the primary peak generated by signals reflected or otherwise returning from the target plane may be substantially less distinctive and the secondary peak may be more prominent in relation to the primary and secondary peaks generated by reflections from the reference plane, the identification of a reference plane and the subsequent indexing of the reference plane to the target point prevents errors that may have arisen in attempts to directly detect the target plane.

Moreover, the embodiments in which the target plane is one of a family of assymetric planes defined by a particular crystal orientation, the measurement of a reference plane and the subsequent location of a target plane based on the reference plane may permit a desired target plane to be identified in an unambiguous manner, thereby preventing additional steps that would otherwise be required in order to identify a particular pair of the assymetric planes. With respect to FIG. 2, for example, assume that the desired pair of target planes are the planes that extend at +54.7° and −125.3°, and not the planes that extend at −54.7° and +125.3°. If attempts were made to directly identify the target plane, the identification of a peak in the radiation reflected or otherwise returning from the crystalline body would not identify which pair of planes had reflected the radiation. However, by directly detecting the reference plane located at 0° and 180° relative to the assymetric planes of FIG. 2, the desired pair of target planes at +54.7° and −125.3° can be unambiguously identified by the predefined angular offset of +54.7° relative to the reference plane. For at least each of the foregoing reasons, the location of a target plane based upon the direct identification of a reference plane is beneficial, irregardless of whether the crystalline body is held by the apparatus of the present invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for orienting a crystalline body during radiation diffractometry, the apparatus comprising:
    a frame comprising:
        a first member adapted to support said frame relative to a source of radiation; and
        a second member movably connected to said first member; and
        an engagement member carried by said second member for engaging a predetermined portion of the crystalline body to thereby define the angle at which incident radiation will impinge upon the crystalline body
    wherein said second member is movably connected to said first member such that movement of said second member relative to said first member alters an angular position of said engagement member with respect to said first member.

2. An apparatus according to claim 1 wherein said frame further comprises a third member for locking said first and second members in position with respect to one another.

3. An apparatus according to claim 1 wherein said first and second members of said frame are rotatably connected.

4. An apparatus according to claim 1 wherein each of said first and second members comprises indicia to facilitate positioning of said first and second members relative to one another.

5. An apparatus according to claim 1 wherein said second member defines an aperture for viewing the engagement of the predetermined portion of the crystalline body by said engagement member.

6. An apparatus according to claim 1 wherein said second member comprises at least one support for engaging another portion of the crystalline body.

7. An apparatus according to claim 1 wherein said first member comprises a base for supporting said frame relative to the source of the radiation.

8. An apparatus according to claim 1 wherein said engagement member is threadably connected to said second member.

9. An apparatus for orienting a crystalline body during radiation diffractometry, the apparatus comprising:
    a frame for supporting at least a portion of the crystalline body during radiation diffractometry, said frame comprising a base adapted to support said frame relative to a source of radiation, said frame also comprising a central portion and at least two arms extending outwardly said central portion, wherein one of said arms is connected to said base; and
    an engagement member carried by another of said arms of said frame for engaging a predetermined portion of the crystalline body, said engagement member extending at a non-orthogonal angle relative to said base.

10. An apparatus according to claim 9 wherein said at least two arms of said frame comprises first, second and third arms extending outwardly from said central portion, wherein said first arm is connected to said base and said third arm carries said engagement member.

11. An apparatus according to claim 10 wherein said third arm defines an axis extending through said central portion and bisecting an angle defined between said first and second arms.

12. An apparatus according to claim 9 wherein said engagement member extends at an angle of 45° with respect to said base.

13. An apparatus according to claim 9 wherein said frame comprises at least one support for engaging another portion of the crystalline body.

14. An apparatus according to claim 9 wherein said engagement member is threadably connected to said frame.

15. A method for orienting a crystalline body during radiation diffractometry, the method comprising:
providing a frame having first and second members movably connected to one another;
positioning the second member of the frame relative to the first member of the frame which is adapted to support said frame relative to a source of radiation; and
engaging a predetermined portion of the crystalline body with an engagement member carried by the second member of the frame to thereby define the angle at which the incident radiation will impinge upon the crystalline body
wherein positioning the second member relative to the first member comprises altering the angular position of the engagement member with respect to the first member.

16. A method according to claim 15 wherein positioning the second member of the frame comprises positioning the second member of the frame relative to the first member of the frame based upon a predefined angular offset between reference and target planes defined by the crystalline body.

17. A method according to claim 15 further comprising locking the first and second members once the second member is positioned relative to the first member.

18. A method according to claim 15 further comprising supporting at least one end of the crystalline body with the frame while the predetermined portion of the crystalline body is engaged with the engagement member.

19. A method according to claim 15 wherein engaging the predetermined portion of the crystalline body with the engagement member comprises threadably advancing the engagement member into engagement with the predetermined portion of the crystalline body.

* * * * *